(12) United States Patent
Ishida et al.

(10) Patent No.: US 12,171,594 B2
(45) Date of Patent: Dec. 24, 2024

(54) DIRECT-CONVERSION X-RAY DETECTOR, METHOD OF DETECTING X-RAY, AND X-RAY COMPUTED-TOMOGRAPHY APPARATUS

(71) Applicant: CANON MEDICAL SYSTEMS CORPORATION, Otawara (JP)

(72) Inventors: Akihiro Ishida, Nasushiobara (JP); Yasuo Saito, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 225 days.

(21) Appl. No.: 18/055,544

(22) Filed: Nov. 15, 2022

(65) Prior Publication Data
US 2023/0148976 A1    May 18, 2023

(30) Foreign Application Priority Data

Nov. 18, 2021    (JP) .................................. 2021-188178

(51) Int. Cl.
*A61B 6/03*    (2006.01)
*G01T 1/24*    (2006.01)
*A61B 6/40*    (2024.01)

(52) U.S. Cl.
CPC .............. *A61B 6/032* (2013.01); *G01T 1/241* (2013.01); *A61B 6/4021* (2013.01)

(58) Field of Classification Search
CPC ..... A61B 6/032; A61B 6/4021; A61B 6/4233; A61B 6/4085; G01T 1/241
See application file for complete search history.

(56) References Cited

U.S. PATENT DOCUMENTS

| | | | | |
|---|---|---|---|---|
| 6,028,313 | A * | 2/2000 | McDaniel | G01T 1/2928 250/370.11 |
| 2005/0023475 | A1* | 2/2005 | Li | H01L 27/14659 378/19 |
| 2007/0280409 | A1* | 12/2007 | Konno | G01T 1/249 378/19 |
| 2013/0256541 | A1* | 10/2013 | Engel | G01T 1/24 438/57 |
| 2017/0285187 | A1* | 10/2017 | Roessl | A61B 6/484 |
| 2020/0138386 | A1 | 5/2020 | Zimmerman et al. | |

FOREIGN PATENT DOCUMENTS

JP    2020-75078 A    5/2020

* cited by examiner

*Primary Examiner* — Kiho Kim
(74) *Attorney, Agent, or Firm* — Oblon, McClelland, Maier & Neustadt, L.L.P.

(57) ABSTRACT

A direct-conversion X-ray detector according to an embodiment includes a plurality of anode electrodes, at least one cathode electrode, and electric-field forming circuitry. The anode electrodes are aligned in a cone angle direction of an incident X-ray. The cathode electrode is positioned on an incident side of an X-ray relative to the anode electrodes, and that opposes the anode electrodes. The electric-field forming circuitry configured to form an electric field in a direction based on a cone angle of the X-ray, between the anode electrodes and the cathode electrode.

9 Claims, 9 Drawing Sheets

DIRECT-CONVERSION X-RAY DETECTOR, METHOD OF DETECTING X-RAY, AND X-RAY COMPUTED-TOMOGRAPHY APPARATUS

CROSS-REFERENCE TO RELATED APPLICATIONS

This application is based upon and claims the benefit of priority from Japanese Patent Application No. 2021-188178, filed on Nov. 18, 2021, the entire contents of which are incorporated herein by reference.

FIELD

Embodiments described herein relate generally to a direct-conversion X-ray detector, a method of detecting an X-ray, and an X-ray computed-tomography apparatus.

BACKGROUND

One problem to be solved by embodiments disclosed in the present specification and the drawings is to reduce deterioration of space resolution in a direction of cone angle of a direct-conversion X-ray detector. Note that problems to be solved by the embodiments disclosed in the present specification and the drawings are not limited to the above problem. Problems corresponding to respective effects obtained by respective components disclosed in the embodiments described later may be regarded as other problems.

DETAILED DESCRIPTION

Figure 1:
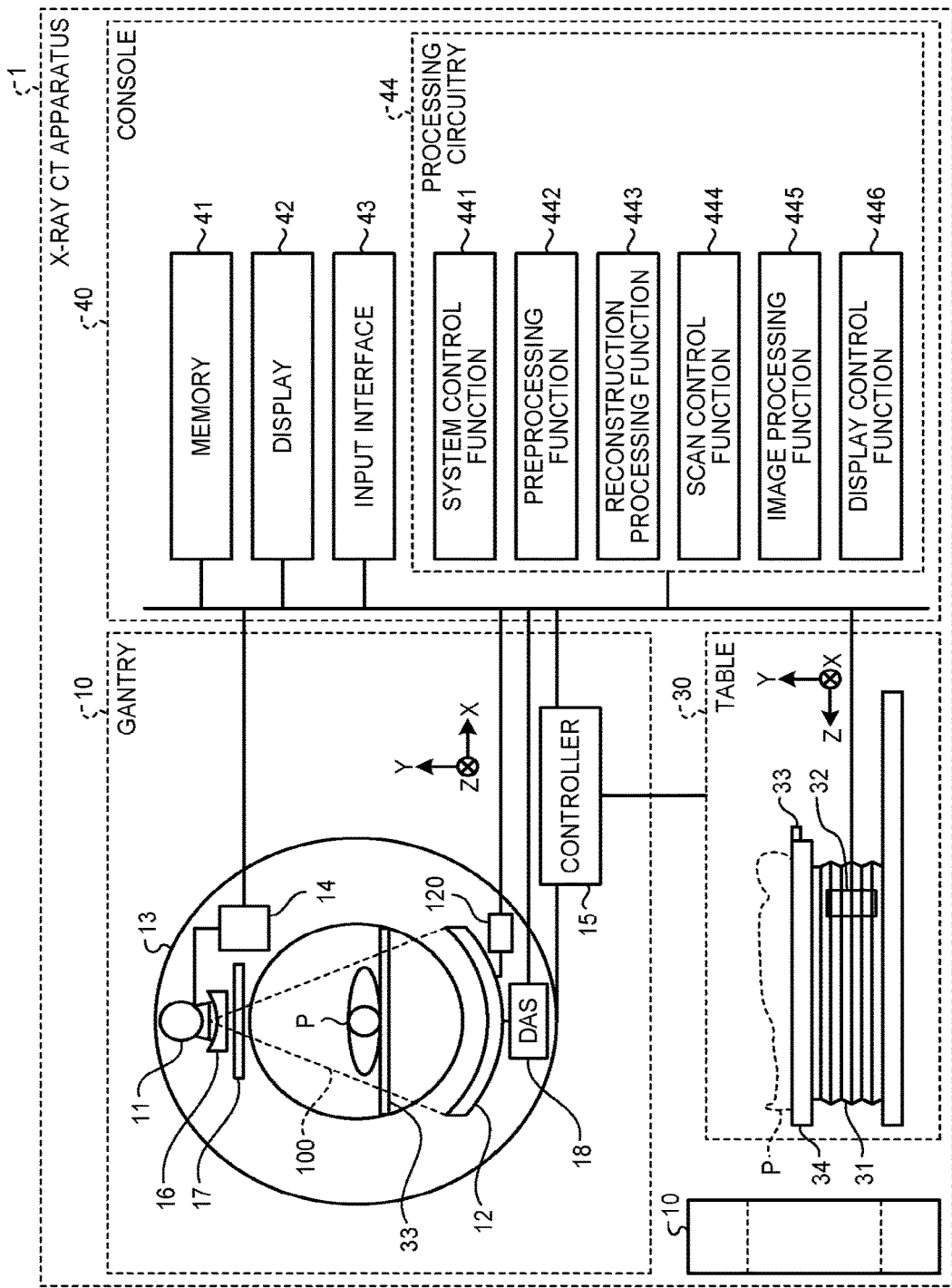
FIG. 1 is a diagram illustrating one example of a configuration of an X-ray CT apparatus according to a first embodiment.

Hereinafter, embodiments of a direct-conversion X-ray detector, a method of detecting an X-ray, and an X-ray computed-tomography apparatus will be explained in detail, referring to the drawings.

First Embodiment

FIG. 1 is a diagram illustrating one example of a configuration of an X-ray computed-tomography (CT) apparatus 1 (hereinafter, "X-ray CT apparatus 1") according to a first embodiment. The X-ray CT apparatus 1 may be referred to as radiation diagnostic-imaging apparatus also.

As illustrated in FIG. 1, the X-ray CT apparatus 1 includes a gantry 10, a table 30, a console 40.

In the present embodiment, a rotation axis of a rotation frame 13 in a non-tilted state or a direction of length of a table 33 of the table 30 is defined as Z-axis direction, an axial direction that is orthogonal to the Z-axis direction, and that is horizontal to a floor surface is defined as X-axis direction, and an axial direction that is orthogonal to the Z-axis, and that is perpendicular to the floor surface is defined as Y-axis direction. Although more than one gantry 10 is illustrated in FIG. 1 for convenience of explanation, only a single unit of the gantry 10 is provided in the actual configuration of the X-ray CT apparatus 1.

The gantry 10 and the table 30 operate based on an operation by a user through the console 40, or based on an operation by a user through an operating unit arranged in the gantry 10 or the table 30. The gantry 10, the table 30, and the console 40 are connected to one another wiredly or wirelessly so that mutual communication is possible.

The gantry 10 is a device including an imaging system that irradiates an X-ray 100 to a subject P, and that collects detection data of the X-ray 100 that has passed through the subject P. More specifically, the gantry 10 includes an X-ray tube 11 (X-ray generating unit), a wedge 16, a collimator 17, an X-ray detector 12, an X-ray high-voltage generator 14, a data acquisition system (DAS) 18, the rotation frame 13, and a controller 15.

The X-ray tube 11 is a vacuum tube that receives application of a high voltage from the X-ray high-voltage generator 14, and supply of a filament current, and that thereby irradiates thermo electrons from an anode (filament) to a cathode (target), to generate the X-ray 100. As the thermo electron collides with a target, the X-ray 100 is generated. The X-ray 100 generated at a focal spot in the X-ray tube 11 is shaped into a cone shape, for example, through the collimator 17, to be irradiated to the subject P. For example, the X-ray tube 11 includes a rotating-cathode X-ray tube that generates an X-ray by irradiating a thermo electron to a rotating cathode.

As illustrated in FIG. 1, the X-ray 100 irradiated in a cone beam shape is to have a shape spreading in a fan shape in the X-axis direction. Accordingly, an angle indicating the spread in the X-axis direction of the X-ray 100 irradiated in a cone beam shape is referred to as fan angle. Moreover, a depth in the Z-axis direction of the X-ray 100 irradiated in the cone beam shape is referred to as cone angle. Therefore, the X-axis direction is also referred to as fan angle direction, and the Z-axis direction is also referred to as cone angle direction.

The X-ray detector 12 detects an X-ray that has been irradiated from the X-ray tube 11 and has passed through the subject P, and outputs an electrical signal corresponding to an amount of the X-ray to the DAS 18.

The X-ray detector 12 has plural rows of detecting devices in which plural detecting devices are aligned in a channel direction along an arc about the focal spot of the X-ray tube 11. Each of the plural detecting devices detects an incident amount of the X-ray 100. The X-ray CT apparatus 1 includes various types, such as a rotate/rotate type (third generation CT) in which the X-ray tube 11 and the X-ray detector 12 rotate around the subject P as an integrated unit, and a stationary/rotate type (fourth generation CT) in which many X-ray detecting devices arrayed in a ring shape are fixed, and in which only the X-ray tube 11 rotates around the subject P, and the like, and any type is applicable to the present embodiment.

More specifically, the X-ray detector 12 is a direct-conversion X-ray detector that has a semiconductor device converting an incident X-ray into an electric charge. The X-ray detector 12 of the present embodiment includes at least one high voltage electrode, at least one semiconductor device, and plural read electrodes. The semiconductor device is also referred to as X-ray conversion device.

Moreover, the X-ray detector 12 includes a potential control device 120 that controls a potential of the high voltage electrode. The potential control device 120 is one example of electric-field forming circuitry in the present embodiment. Details of a configuration of the X-ray detector 12 is described later.

Furthermore, the X-ray detector 12 according to the present embodiment may be of energy-integrated collection system, or of photo-counting collection system.

The rotation frame 13 supports the X-ray tube 11 and the X-ray detector 12 rotatably about a rotation axis. Specifically, the rotation frame 13 is a ring-shaped frame that supports the X-ray tube 11 and the X-ray detector 12 in an opposing manner, and that rotates the X-ray tube 11 and the X-ray detector 12 by the controller 15 described later. The rotation frame 13 is rotatably supported by a fixing frame that is made from metal, such as aluminum. The rotation frame 13 rotates about the rotation axis at a uniform angular speed, receiving a power from a driving mechanism of the controller 15.

The rotation frame 13 further supports the X-ray high-voltage generator 14 and the DAS 18 in addition to the X-ray tube 11 and the X-ray detector 12. The rotation frame 13 as described is housed in casing in a substantially cylindrical shape in which an opening (bore) to form imaging space is formed. A center axis of the opening coincides with the rotation axis of the rotation frame 13.

The X-ray high-voltage generator 14 includes an electric circuitry such as a transformer and a rectifier, and includes a high-voltage generating device having a function of generating a high voltage to be applied to the X-ray tube 11 and a filament current to be supplied to the X-ray tube 11, and an X-ray control device that controls an output voltage according to an X-ray to be irradiated by the X-ray tube 11. The high-voltage generating device may be of transformer type, or may be of inverter type. The X-ray high-voltage generator 14 may be arranged in the rotation frame 13, or may be arranged on the fixing frame (not illustrated) side of the gantry 10. The fixing frame is a frame rotatably supporting the rotation frame 13.

The controller 15 includes a processing circuitry having a central processing unit (CPU) and the like, and a driving mechanism, such as a motor and an actuator. The processing circuitry includes, as hardware resources, a processor, such as a CPU and a microprocessor unit (MPU), and a memory, such as a read-only memory (ROM) and a random access memory (RAM). Moreover, the controller 15 may be implemented by a processor, such as a graphics processing unit (GPU), an application specific integrated circuit (ASIC), a programmable logic device (for example, simple programmable logic device (SPLD), complex programmable logic device (CPLD)), and a field programmable gate array (FPGA). For example, when the processor is CPU, the processor implements a function by reading and executing a program stored in a memory. On the other hand, when the processor is ASIC, instead of storing a program in a memory, the function is directly installed in a circuit of the processor as a logic circuit. Respective processors of the present embodiment are not limited to be configured as a single circuit per processor, but plural independent circuits may be combined as one processor, to implement the function. Furthermore, plural components may be integrated into a single processor, to implement the function.

Furthermore, the controller 15 has a function of controlling operation of the gantry 10 and the table 30 by receiving an input signal from an input interface 43 that is attached to the console 40 or the gantry 10. For example, receiving the input signal, the controller 15 performs control of rotating the rotation frame 13, a control of tilting the gantry 10, a control of operating the table 30 and the table 33. The control of tilting the gantry 10 may be implemented by rotating the rotation frame 13 about an axis parallel to the X-axis direction by the controller 15 based on inclination angle (tilt angle) information input by the input interface 43 attached to the gantry 10. Moreover, the controller 15 may be arranged in the gantry 10, or may be arranged in the console 40.

The wedge 16 is a filter to adjust an X-ray dosage of the X-ray 100 irradiated by the X-ray tube 11. Specifically, the wedge 16 is a filter that attenuates the X-ray 100 irradiated by the X-ray tube 11 as it passes therethrough so that the X-ray 100 to be irradiated to the subject P from the X-ray tube 11 has a predetermined distribution. The wedge 16 is, for example, wedge filter or bow-tie filter, and is a filter formed by processing aluminum to obtain a predetermined target angle or a predetermined thickness.

The collimator 17 is a lead plate or the like to narrow the X-ray 100 that has passed through the wedge 16 into an X-ray irradiation range, and forms a slit by combination of plural lead plates or the like.

The DAS 18 includes an amplifier that performs amplification processing with respect to an electrical signal output from the respective X-ray detecting devices of the X-ray detector 12, and an A/D converter that converts an electrical signal into a digital signal, and generates detection data. The detection data generated by the DAS 18 is transferred to the console 40. Moreover, the DAS 18 is one example of a data collecting unit.

In the present embodiment, when simply referring to "detection data", it signifies both pure raw data that is data detected by the X-ray detector 12 before subjected to the preprocessing, and raw data that is obtained by subjecting the pure raw data to the preprocessing. Note that data before preprocessing (detection data) and data after preprocessing can be denoted as projection data collectively.

The table 30 is a device on which the subject P to be scanned is placed and that moves the subject P, and includes a base 31, a table driving device 32, the table 33, and a table supporting frame 34. The base 31 is a casing that supports the table supporting frame 34 movably in a vertical direction. The table driving device 32 is a motor or an actuator that moves the table 33 on which the subject P is placed in a direction of longitudinal axis of the table 33. The table driving device 32 moves the table 33 according to a control by the console 40 or the controller 15. The table 33 arranged on an upper surface of the table supporting frame 34 is a plate on which the subject P is placed. The table driving device 32 may move the table supporting frame 34 in a direction of the longitudinal axis of the table 33, in addition to the table 33.

The console 40 is a device that performs a control of the gantry 10, generation of CT image data based on a scan result by the gantry 10, and the like. The console 40 includes a memory 41 (storage unit), a display 42 (display unit), an input interface 43 (input unit), and processing circuitry 44 (processing unit). Data communication among the memory 41, the display 42, the input interface 43, and the processing circuitry 44 is performed through a bus.

The memory 41 is implemented, for example, by a semiconductor memory device, such as a RAM and a flash memory, a hard disk drive (HDD), a solid state drive (SSD), an optical disk, or the like. Moreover, the memory 41 may also be a driving device that reads and writes various kinds of information between a portable storage medium, such as a compact disc (CD), a digital versatile disc (DVD), and a flash memory, and a semiconductor memory, such as a RAM, or the like. The memory 41 stores, for example, projection data and reconstructed image data. Furthermore, a storage area of the memory 41 may be in the X-ray CT apparatus 1, or may be in an external storage device connected through a network. Moreover, the memory 41 stores a control program according to the present embodiment. Furthermore, the memory 41 is one example of a storage unit.

The display 42 displays various kinds of information. For example, the display 42 outputs a medical image (CT image) generated by the processing circuitry 44, a graphical user interface (GUI) to accept various kinds of operations from an operator, and the like. For example, as the display 42, a liquid crystal display (LCD), an organic electroluminescence display (OELD), a plasma display, or other arbitrary displays can be used appropriately. Moreover, the display 42 may be arranged in the gantry 10. The display 42 may be of desktop type, or may be configured with a tablet terminal that can communicate with the console 40 wirelessly, or the like.

The input interface 43 accepts various kinds of input operations from an operator, and converts the accepted input operation into an electrical signal, to output to the processing circuitry 44. For example, the input interface 43 accepts a collection condition when projection data is collected, a reconstruction condition when a CT image is reconstructed, an image processing condition when a post processing image is generated from a CT image, and the like from an operator. As the input interface 43, for example, a mouse, a keyboard, a trackball, a switch, a button, a joystick, a touch pad, a touch panel display, and the like can be appropriately used.

In the present embodiment, the input interface 43 is not limited to ones having a physical operating part, such as a mouse, a keyboard, a trackball, a switch, a button, a joystick, a touchpad, and a touch panel display. For example, processing circuitry of an electrical signal that receives an electrical signal corresponding to an input operation from an external input device arranged separately from the device, and that outputs this electrical signal to the processing circuitry 44 is also included in examples of the input interface 43. Furthermore, the input interface 43 is one example of an input unit. The input interface 43 may be arranged in the gantry 10. Moreover, the input interface 43 may be configured with a tablet terminal that is capable of wireless communication with the console 40.

The processing circuitry 44 controls overall operation of the X-ray CT apparatus 1 according to an electrical signal of an input operation output from the input interface 43. For example, the processing circuitry 44 includes a system control function 441, a preprocessing function 442, a reconstruction processing function 443, a scan control function 444, an image processing function 445, and a display control function 446. For example, respective processing functions performed by the system control function 441, the preprocessing function 442, the reconstruction processing function 443, the scan control function 444, the image processing function 445, and the display control function 446, which are components of the processing circuitry 44 illustrated in FIG. 1 are stored in the memory 41 in a form of computer-executable program. The processing circuitry 44 is, for example, a processor, and reads respective programs from the memory 41, and implements functions corresponding to the read programs by executing the programs. In other words, the processing circuitry 44 that has read the respective programs is to have the respective functions illustrated in the processing circuitry 44 in FIG. 1. The system control function 441 is one example of a control unit. The preprocessing function 442 is one example of the preprocessing unit. The reconstruction processing function 443 is one example of a reconstruction processing unit. The scan control function 444 is one example of the scan control unit. The image processing function 445 is one example of the image processing unit. The display control function 446 is one example of a display control unit. Moreover, the processing circuitry 44 may be one example of the control unit.

Although a case in which the system control function 441, the preprocessing function 442, the reconstruction processing function 443, the scan control function 444, and the display control function 446 are implemented by a single unit of the processing circuitry 44 is illustrated in FIG. 1, but embodiments are not limited thereto. For example, the processing circuitry 44 may be configured by combining plural independent processors, and may implement the respective processing functions by executing the respective programs by the respective processors. Furthermore, the respective processing functions included in the processing circuitry 44 may be implemented by a single or plural processing circuits in a distributed or integrated manner.

The system control function 441 controls the respective functions of the processing circuitry 44 based on an input operation accepted from an operator through the input interface 43.

The preprocessing function 442 generates data obtained by subjecting detection data output from the DAS 18 to preprocessing, such as logarithmic conversion processing, offset correction processing, sensitivity correction processing among channels, and beam hardening correction.

The reconstruction processing function 443 generates CT image data by performing reconstruction processing using the filtered back-projection method, the successive approximation construction method, and the like with respect to projection data generated by the preprocessing function 442.

The scan control function 444 acquires two-dimensional positioning image data of the subject P to determine a scan range, an imaging condition, and the like. The positioning image data is also referred to as scanno-image data or scout image data.

The image processing function 445 converts the CT image data generated by the reconstruction processing function 443 by a publicly known method into tomography data of an arbitrary section or three-dimensional image data based on an input operation accepted from an operator through the input interface 43. Generation of three-dimensional image may be performed by the reconstruction processing function 443 directly.

The display control function 446 causes the display 42 to display the tomography image and the three-dimensional image processed by the image processing function 445. Moreover, the display control function 446 causes the display 42 to display various kinds of GUI.

Figure 2:
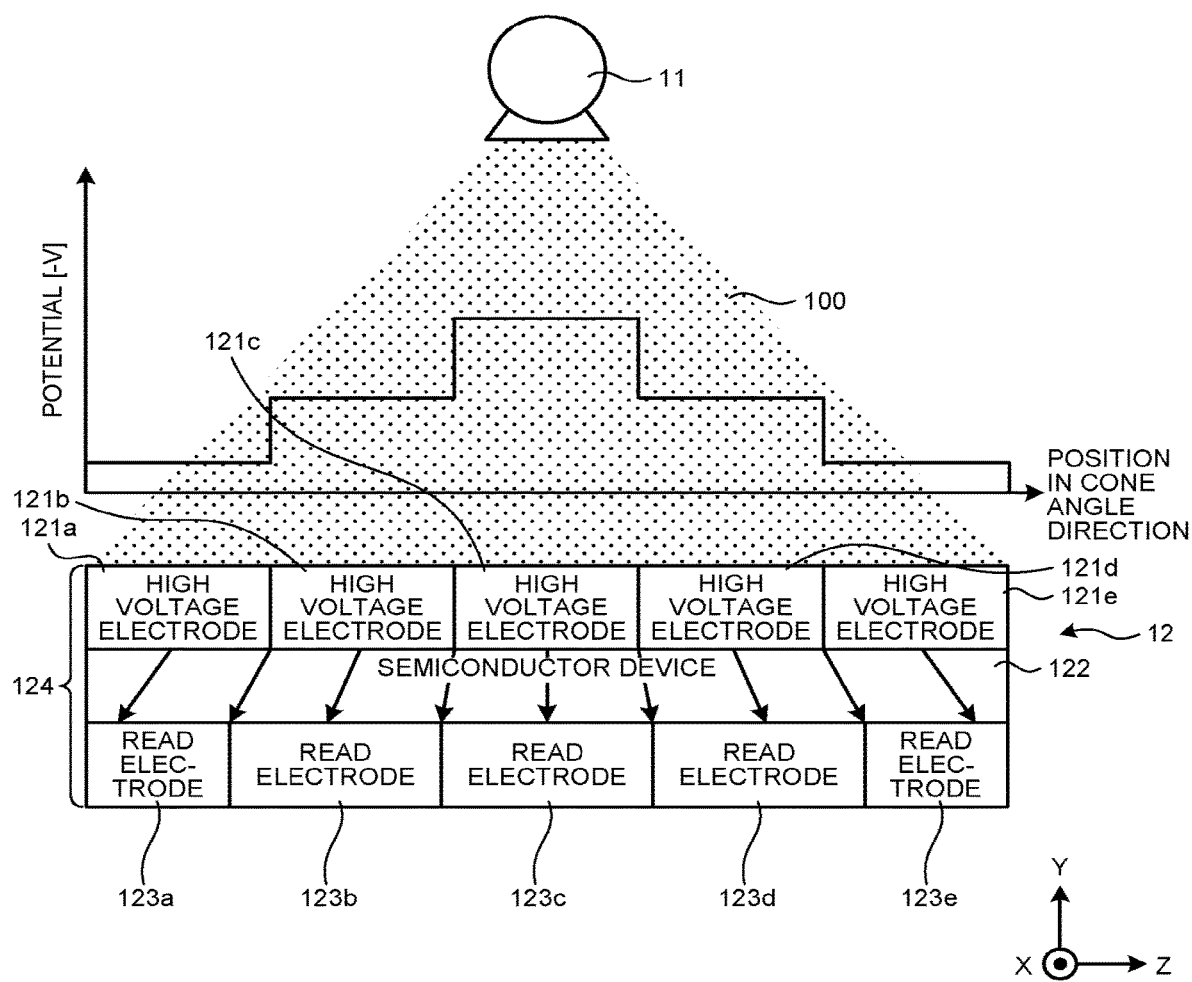
FIG. 2 is a diagram illustrating one example of a configuration of an X-ray detector according to the first embodiment.

Next, details of the X-ray detector 12 will be explained. FIG. 2 is a diagram illustrating one example of a configuration of the X-ray detector 12 according to the first embodiment. FIG. 2 illustrates a state in which the X-ray detector 12 is viewed from the X-axis direction.

The X-ray detector 12 includes plural high voltage electrodes 121a to 121e, one semiconductor device 122, and plural read electrodes 123a to 123e. The plural high voltage electrodes 121a to 121e, the semiconductor device 122, and the plural read electrodes 123a to 123e constitute one detection module 124. The X-ray detector 12 includes plural detection modules 50 in a fan angle direction. The number of the high voltage electrodes 121a to 121e and the read electrodes 123a to 123e included in one detection module 124 is not limited to the example illustrated in FIG. 2.

Hereinafter, when the respective high voltage electrodes 121a to 121e are not distinguished from one another, it is denoted simply as high voltage electrode 121. Moreover, the respective read electrodes 123a to 123e are not distinguished from one another, it is denoted simply as read electrode 123.

Moreover, in an upper part in FIG. 2, a graph showing a distribution of potential of the high voltage electrodes 121a to 121e of each position in the cone angle direction of an X-ray incident on the X-ray detector 12 is illustrated. Because the high voltage electrodes 121a to 121e have a negative potential, the unit of the vertical axis of the graph is "−V".

In the present embodiment, in one detection module 124, the plural read electrodes 123a to 123e and the plural high voltage electrodes 121a to 121e are respectively aligned in the cone angle direction of the X-ray 100.

In the X-ray detector 12, the plural detection modules 124 are aligned in a curved shape in the fan angle direction. Therefore, the shape of the X-ray detector 12 is an arc-shaped plane in the fan angle direction. Moreover, the shape of the X-ray detector 12 is a flat plane in the cone angle direction. Therefore, in the X-ray detector 12, at a portion having a larger cone angle, an incident angle of the X-ray 100 with respect to the semiconductor device 122 is larger.

The high voltage electrodes 121a to 121e are positioned on an incidence side of the X-ray 100 relative to the read electrodes 123a to 123e, and oppose to the read electrodes 123a to 123e. The high voltage electrodes 121a to 121e are one example of a cathode electrode in the present embodiment. The high voltage electrodes 121a to 121e are aligned along the cone angle direction of the incident X-ray 100.

The semiconductor device 122 is positioned between the high voltage electrodes 121a to 121e and the read electrodes 123a to 123e, and converts the X-ray 100 incident from the high voltage electrodes 121a to 121e side into an electric charge.

The read electrodes 123a to 123e read the electric charge converted from the X-ray 100 by the semiconductor device 122 as an electrical signal. The electrical signal read by the read electrodes 123a to 123e is amplified by the DAS 18, to be converted into a digital signal, and is transferred to the console 40 as detection data. The read electrodes 123a to 123e are one example of an anode electrode in the present embodiment. Reading of an electric charge by the read electrodes 123a to 123e is also expressed as collection of an electric charge.

The high voltage electrodes 121a to 121e have a negative potential, and the read electrodes 123a to 123e have a positive potential. By a potential difference between the high voltage electrodes 121a to 121e and the read electrodes 123a to 123e, the electric charge converted from the X-ray by the semiconductor device 122 moves to the read electrodes 123a to 123e. Between the high voltage electrodes 121a to 121e and the read electrodes 123a to 123e, an electric field is formed.

More specifically, the electric field between the high voltage electrodes 121a to 121e and the read electrodes 123a to 123e is formed by a set of electric fields formed by a great number of point charges. A distribution of size and density of the respective point charges determines a direction of the electric field as a whole.

Moreover, in the present embodiment, the potential control device 120 controls each of the high voltage electrodes 121a to 121e such that the high voltage electrode 121 positioned farther from the center (midplane) in the cone angle direction has a higher potential out of the high voltage electrodes 121a to 121e aligned in the cone angle direction of the incident X-ray 100. For example, the potential control device 120 applies different voltages to the plural high voltage electrodes 121a to 121e depending on a position along the cone angle direction, to thereby generate an electric field in a direction based on a cone angle. The potential control device 120 receives a supply of power from a power source device not illustrated.

As illustrated in FIG. 2, a potential of the high voltage electrode 121c positioned at a center of the cone angle direction is the lowest, and a potential of the high voltage electrode 121a and the high voltage electrode 121e positioned at end portions in the cone angle direction are the highest.

Specific values of potential of the plural high voltage electrodes 121a to 121e are not particularly limited, but are determined according to a length of the Z-axis direction of the X-ray detector 12, the size of the cone angle of the X-ray 100, and the like. The polarity of the high voltage electrodes 121a to 121e, the number of the high voltage electrodes 121a to 121e, and the like may be changed according to characteristics of the X-ray detector 12.

Note that even the potential of the high voltage electrodes 121a and 121e that are the highest among the plural high voltage electrodes 121a to 121e is lower than a potential of the read electrodes 123a to 123e. Moreover, the potentials of the plural high voltage electrodes 121a to 121e are uniform.

Specifically, the direction of the electric field between the high voltage electrodes 121a to 121e and the read electrodes 123a to 123e is a direction straight ahead from the high voltage electrode 121c toward the read electrode 123c in a center area in the cone angle direction of the X-ray detector 12. Moreover, the direction of the electric field is directed more toward the opposite side to the center of the cone angle direction of the X-ray detector 12 at a position farther away from the center of the cone angle direction of the X-ray detector 12. Therefore, the direction of the electric field between the high voltage electrodes 121a to 121e and the read electrodes 123a to 123e is to be a direction based on the cone angle of the X-ray 100. Because an electric charge moves along a direction of an electric field, the electric charge converted from the X-ray 100 by the semiconductor device 122 moves toward the read electrodes 123a to 123e along a direction based on the cone angle of the X-ray 100.

The direction of the electric field between the high voltage electrodes 121a to 121e and the read electrodes 123a to 123e is inclined so as to spread symmetrically toward the both end portions with respect to a center in the cone angle direction straight from the X-ray tube 11. The direction of the electric field may be not completely equal to the cone angle of the X-ray 100, as long as at least the direction of inclination is the same.

For example, an electric charge converted from the X-ray 100 from the X-ray tube 11 traveling straight and incident on the high voltage electrode 121c of the X-ray detector 12 continues to travel straight along the direction of the electric field, and moves to the read electrode 123c. In this case, the electric charge converted from the X-ray 100 incident on the high voltage electrode 121c is read as an electrical signal from the read electrode 123c. Moreover, an electric charge converted from the X-ray 100 incident on the high voltage electrode 121e moves diagonally along the direction of the electric field, and moves to the read electrode 123e. Therefore, the electric charge converted from the X-ray 100 incident on the same high voltage electrode 121 is read by the same read electrode 123.

A relationship between a direction of an electric field and reading of an electric charge will be explained in detail by using FIG. 3 and FIG. 4.

First, a configuration of a general X-ray detector will be explained as a comparative example.

Figure 3:
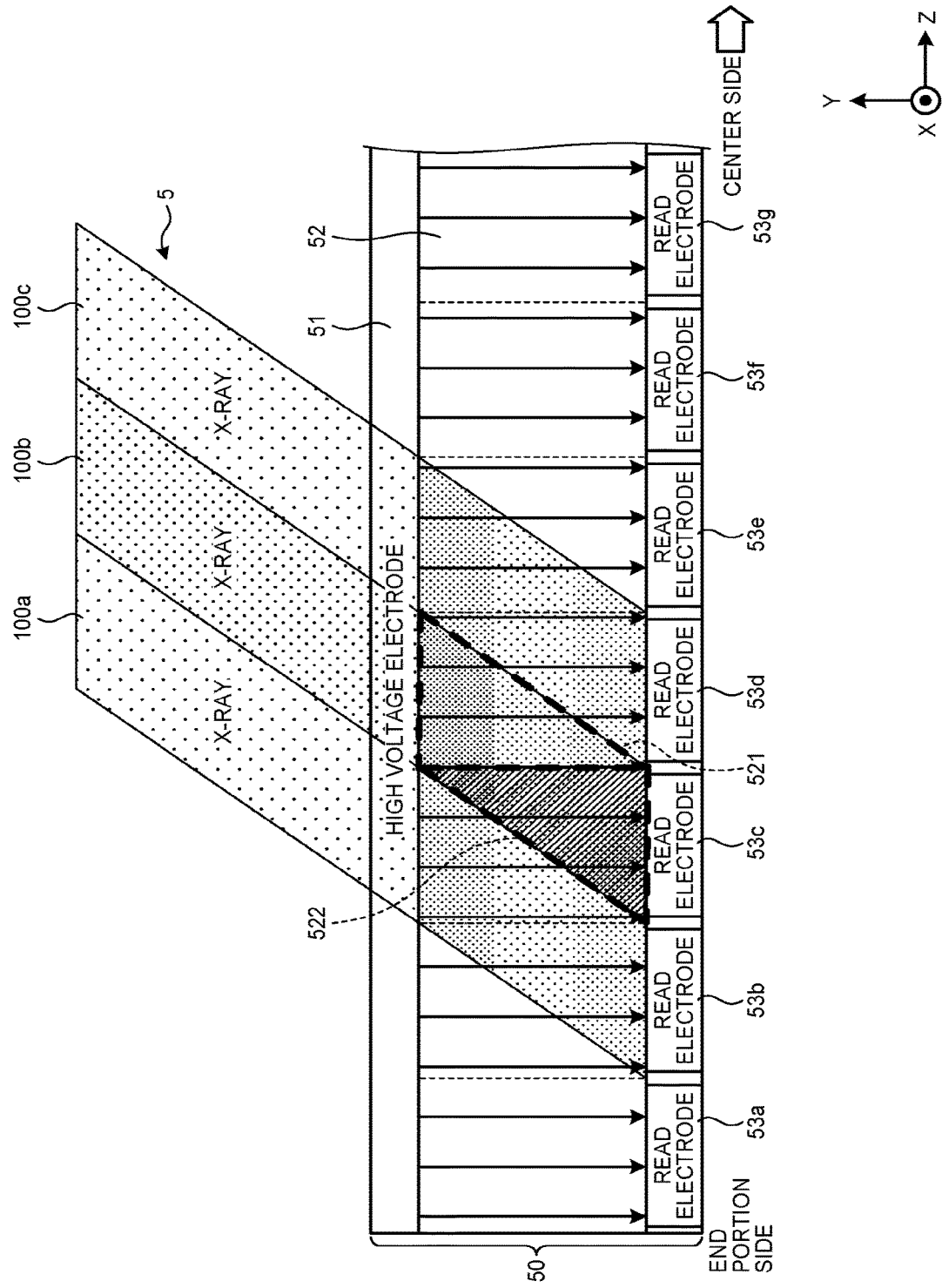
FIG. 3 is a diagram illustrating one example of a configuration of an X-ray detector according to a comparative example.

FIG. 3 is a diagram illustrating an example of a configuration of an X-ray detector 5 according to a comparative example. FIG. 3 illustrates a state in which a part of the X-ray detector 5 according to the comparative example is viewed from the X-axis direction. A right side in FIG. 3 is a center side in a cone angle direction in the X-ray detector 5, and a left side in FIG. 3 is an end portion side.

The X-ray detector 5 according to the comparative example includes a high voltage electrode 51, a semiconductor device 52, and plural read electrodes 53a to 53g. A set of the high voltage electrode 51, the semiconductor device 52, and the plural read electrodes 53a to 53g is referred to as one detection module 50. The X-ray detector 5 includes plural units of the detection modules 50. When the respective read electrodes 53a to 53g are not particularly distinguished from one another, it is denoted simply as read electrode 53.

In the present comparative example, in one detection module 50, a single unit of high voltage electrode 51 is included. In the high voltage electrode 51 in the present comparative example, there is no potential difference in the cone angle direction, and it is constant. Therefore, the direction of the electric field between the high voltage electrode 51 and the plural read electrodes 53a to 53g is straight from the high voltage electrode 51 toward the read electrodes 53a to 53g.

X-rays 100a to 100c incident on the high voltage electrode 51 are converted into an electric charge by the semiconductor device 52, but because a position in the Y-axis direction of the semiconductor device 52 at which the X-ray 100a to 100c are absorbed is statistically random, the control is difficult.

For example, in the example illustrated in FIG. 3, the X-ray 100b incident on the high voltage electrode 51 is absorbed in a first area 521 or a second area 522 of the semiconductor device 52. Out of the X-ray 100b, an electric charge converted from a portion absorbed in the first area 521 of the semiconductor device 52 moves to the read electrode 53d along a direction of the electric field, and is read from the read electrode 53d. Moreover, out of the X-ray 100b, an electric charge converted from a portion absorbed in the second area 522 of the semiconductor device 52 moves to the read electrode 53c along the direction of the electric field, and is read from the read electrode 53c. That is, in the comparative example, a part of the electric charges converted from the X-ray 100b incident on the same position in the high voltage electrode 51 is read from the read electrode 53d, and another part thereof is read by the read electrode 53c adjacent to the read electrode 53d. Similarly, electric charges converted from the X-rays 100a, 100c incident on another position of the high voltage electrode 51 are read separately by the plural adjacent read electrodes 53.

Generally, as the reconstruction theory of the detected X-ray 100, it is regarded that the X-ray 100 has entered at a position on a surface of the semiconductor device 52 where the X-ray 100 has entered. However, in the case of oblique incidence of the X-ray 100, the X-ray 100 can be absorbed, not limited to the semiconductor device 52 where the X-ray 100 has entered, but also by another semiconductor device adjacent thereto. This can cause deterioration of space resolution in the cone angle direction of the X-ray detector 5, and it can be factor in degradation of image quality of X-ray image data. Particularly, because the X-ray conversion device that is used in the direct-conversion X-ray detector that directly converts the X-ray 100 into an electric charge is generally thicker than the X-ray conversion device that is used in the indirect conversion X-ray detector, it is more likely to be affected by oblique incidence of an X-ray.

On the other hand, in the X-ray detector 12 of the present embodiment, the direction of the electric field between the high voltage electrode 121 and the read electrode 123 is inclined along the cone angle of the X-ray 100, unlike the X-ray detector 5 of the comparative example. Accordingly, when the X-ray 100 enters the X-ray detector 12 obliquely, an electric charge converted from the X-ray 100 obliquely incident moves in the same direction as the X-ray 100 obliquely incident.

Figure 4:
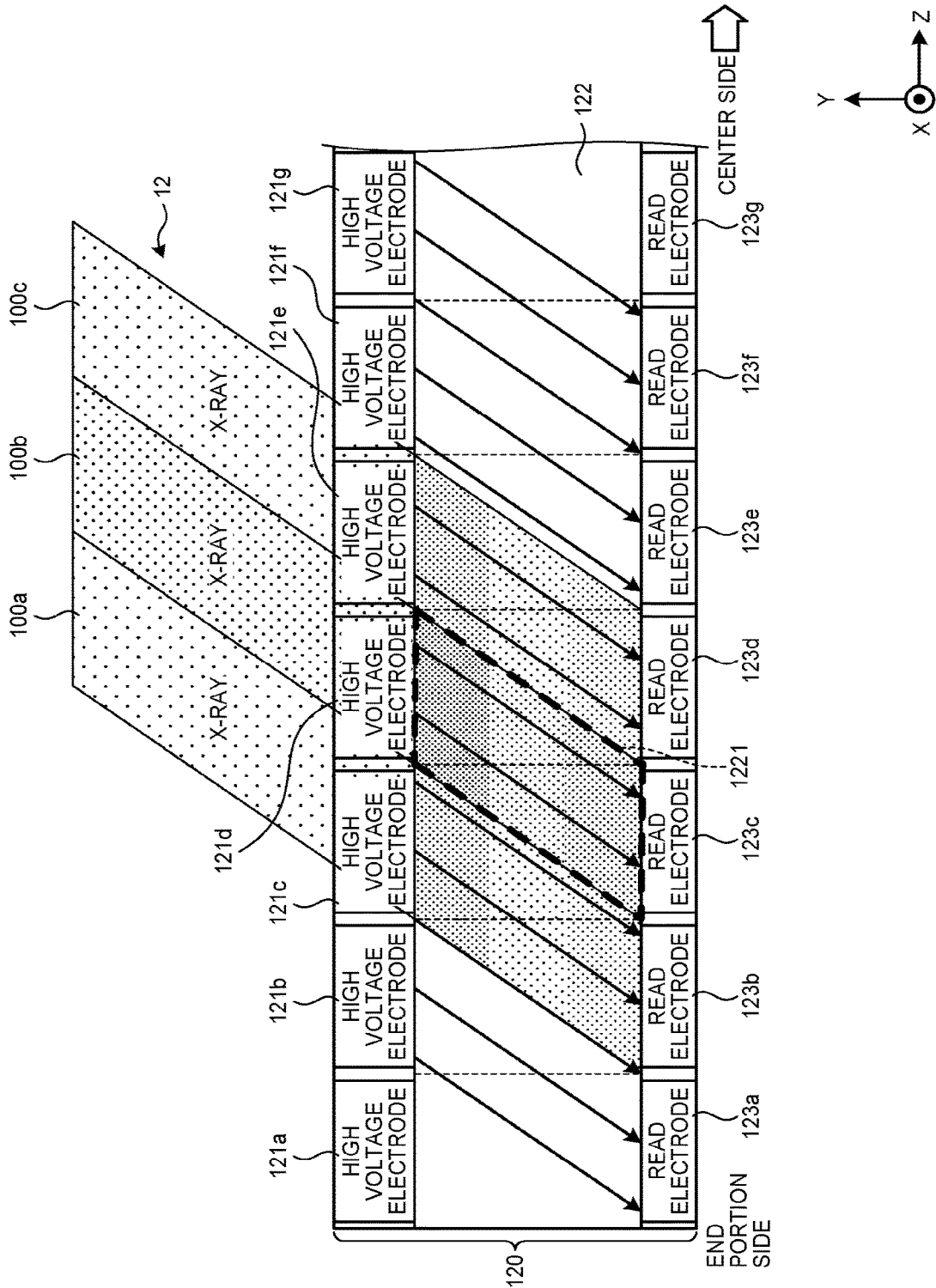
FIG. 4 is a diagram illustrating one example of a direction of electric field of the X-ray detector according to the first embodiment in detail.

FIG. 4 is a diagram illustrating one example of a direction of the electric field of the X-ray detector 12 according to the first embodiment in detail. A right side in FIG. 4 is a center side in the cone angle direction in the X-ray detector 12, and a left side in FIG. 4 is an end portion side.

The number of the high voltage electrode 121 and the read electrode 123 included in the detection module 124 of the X-ray detector 12 illustrated in FIG. 4 differ from those in the example illustrated in FIG. 2, but the detection modules 124 illustrated in FIG. 2 and FIG. 4 are both one example, and the number of the high voltage electrode 121 and the read electrode 123 is not limited thereto.

As illustrated in FIG. 4, in the X-ray detector 12 according to the first embodiment, an electric charge moves obliquely in the same direction as the cone angle of the X-ray 100 by the inclination of the direction of the electric field between the high voltage electrodes 121a to 121g and the read electrodes 123a to 123g.

For example, the X-ray 100b incident on the high voltage electrode 121d is absorbed in an area 1221 of the semiconductor device 122. The X-ray 100b absorbed in the area 1221 of the semiconductor device 122 is converted in to an electric charge by the semiconductor device 122. The electric charge converted from the X-ray 100b moves in a direction apart from the center along the direction of the electric field, and is read by the read electrode 123c. In the X-ray detector 12 of the present embodiment, an electric charge based on the X-ray 100b incident on the high voltage electrode 121d is all read by the read electrode 123c regardless of a position in a depth direction of the semiconductor device 122 at which it is absorbed.

Furthermore, an electric charge based on the X-ray 100a incident on the high voltage electrode 121c is all read by the read electrode 123b. An electric charge based on the X-ray 100c incident on the high voltage electrode 121e is all read by the read electrode 123*d*. That is, in the X-ray detector 12 of the present embodiment, out of the high voltage electrodes 121*a* to 121*g* included in the detection module 124, an electric charge based on the X-ray 100 incident on the same high voltage electrode 121 is read by the same read electrode 123. Moreover, as illustrated in FIG. 4, the X-ray 100 incident on the high voltage electrode 121 is read by the read electrode 123 that is present at a position shifted toward a direction apart from the center position of the X-ray detector 12 along the cone angle direction (Z-axis direction) from the incident position on the high voltage electrode 121. The gap between the incident position and the read electrode 123 changes according to a size of the cone angle and the incident position. The read electrode 123 is arranged at a position, considering the position gap. In FIG. 4, the read electrodes 123*b* to 123*d* are arranged in one to one correspondence respectively with the high voltage electrodes 121*c* to 121*e*, but this configuration is one example, and the relationship between the read electrodes 123*b* to 123*d* and the high voltage electrodes 121*c* to 121*e* is not necessarily required to be in one to one correspondence.

In other words, projection data based on an electric charge read by the read electrode 123*c* is based on the X-ray 100*b* incident on the X-ray detector 12 from the position of the high voltage electrode 121*d*. As for projection data based on an electric charge read by the other read electrode 123 also, it is possible to uniquely identify which one of the X-ray 100 that has entered from which position of which one of the high voltage electrodes 121 in the X-ray detector 12 it is based on.

Therefore, when the reconstruction processing function 443 of the processing circuitry 44 reconstructs projection data, the reconstruction processing can be performed according to the actual correspondence between the high voltage electrodes 121*a* to 121*g* and the read electrodes 123*a* to 123*g*.

Next, a flow of detection of the X-ray 100 in the X-ray CT apparatus 1 of the present embodiment configured as described above will be explained.

Figure 5:
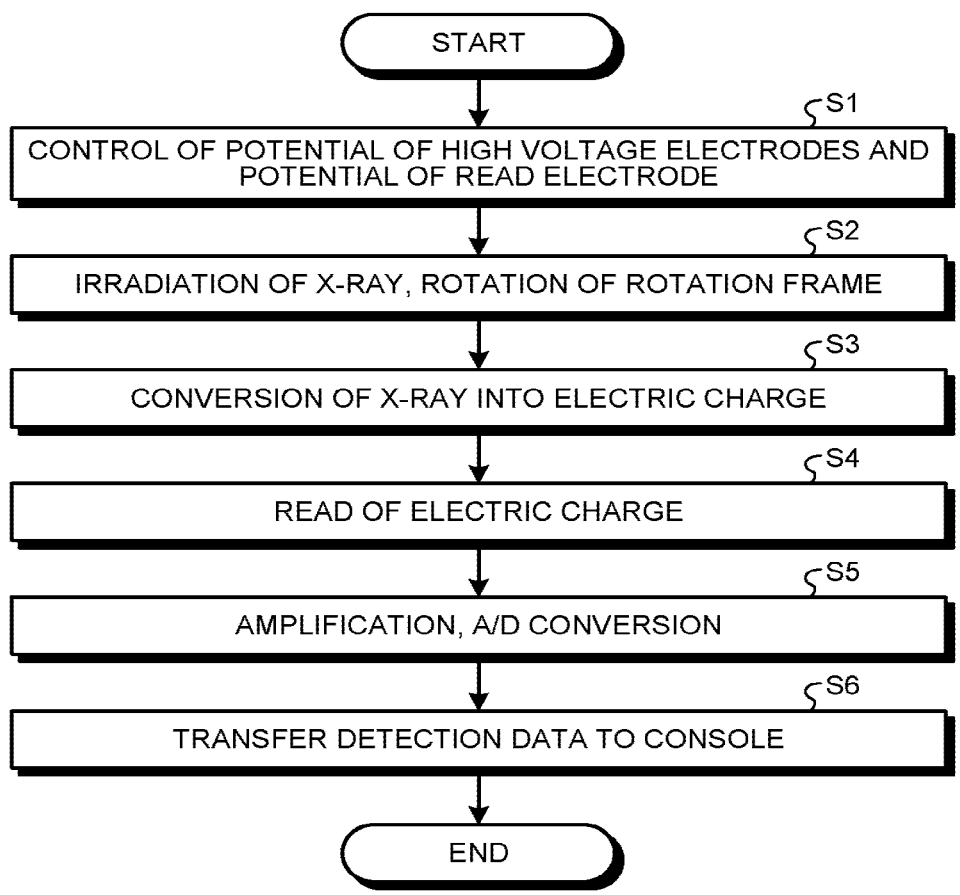
FIG. 5 is a flowchart illustrating one example of a flow of detecting an X-ray in the X-ray CT apparatus according to the first embodiment.

FIG. 5 is a flowchart illustrating an example of a flow of detection of the X-ray 100 in the X-ray CT apparatus 1 according to the first embodiment. The flow of processing in this flowchart is common between imaging for positioning and real imaging. The processing of this flowchart is performed when an operation of starting imaging is performed through the input interface 43 of the console 40 by a technician or the like, for example, in a state in which the subject P is placed on the table 33. Moreover, in explanation of FIG. 5, the configuration of the X-ray detector 12 explained in FIG. 2 is explained as an example.

First, the potential control device 120 controls the respective high voltage electrodes 121*a* to 121*e* such that a potential is higher in the high voltage electrode 121 farther away from the center in the cone angle direction out of the high voltage electrodes 121*a* to 121*e* included in the respective plural detection modules 124 in the X-ray detector 12. Furthermore, the potential control device 120 controls potentials of the read electrodes 123*a* to 123*e* included respectively in the plural detection modules 124 in the X-ray detector 12 (S1).

By such a potential control, the direction of the electric field between the high voltage electrodes 121*a* to 121*e* and the read electrodes 123*a* to 123*e* is to be a direction spreading toward the both end portions from the center of the X-ray detector 12 similarly to the cone angle of the X-ray 100.

The potentials of the read electrodes 123*a* to 123*e* included respectively in the plural detection modules 124 are all uniform positive potential. Because the potential of the read electrodes 123 is uniform, it may be configured to maintain the same potential all the time without being controlled by the potential control device 120.

The X-ray tube 11 generates the X-ray 100 by receiving application of a high voltage from the X-ray high-voltage generator 14, and supply of a filament current. The X-ray 100 generated at the focal spot in the X-ray tube 11 is shaped into a cone beam through, for example, the collimator 17, to irradiated to the subject P. Moreover, the rotation frame 13 rotates around the subject P in a state holding the X-ray tube 11 and the X-ray detector 12 (S2).

The X-ray 100 irradiated from the X-ray tube 11 enters the X-ray detector 12. The semiconductor device 122 of the X-ray detector 12 converts the incident X-ray 100 into an electric charge (S3).

The respective read electrode 123*a* to 123*e* corresponding to the high voltage electrodes 121*a* to 121*e* read the electric charge converted from the X-ray 100 as an electrical signal (S4).

The DAS 18 amplifies the electrical signal read by the read electrode 123 of the X-ray detector 12, and then A/D converts it into a digital signal (S5).

The DAS 18 transfers the signal converted in to a digital signal to the console 40 as detection data (S6). At this point, the processing of this flowchart ends. In this flowchart, illustration of the preprocessing, the reconstruction processing, and the like of the detection data performed by the console 40 is omitted.

As described, the X-ray detector 12 of the present embodiment includes the plural read electrodes 123 that are aligned in the cone angle direction of the incident X-ray 100, the plural high voltage electrodes 121 that are positioned on the incidence side of the X-ray 100 relative to the plural read electrodes 123, and that oppose to the read electrodes 123, and the potential control device 120 that forms an electric field in a direction based on the cone angle between the plural read electrodes 123 and the read electrode 123. Therefore, according to the X-ray detector 12 of the present embodiment, by reducing phenomenon in which the X-ray 100 incident on the same position are read by the different read electrodes 123, deterioration of space resolution in the cone angle of the X-ray detector 12 can be reduced.

More specifically, according to the X-ray detector 12 of the present embodiment, because the X-ray 100 incident on the same position is read by the same read electrode 123, it is possible to match the incident position in the reconstruction theory and an actual incident position when projection data based on the detection data read by the read electrode 123 is reconstructed, and deterioration of space resolution in the cone angle of reconstructed CT image data can be reduced.

As another method of reducing deterioration of space resolution in the cone angle, there is a comparative example in which the detection module is arranged to be an alignment of smaller modules, and a plane is directed to the X-ray incident direction in a unit of each small module. In this case, each of the small modules can be directed to a direction according to the cone angle direction. However, by adopting this structure, scatter rays originated from the structure of the small modules can occur or the like, to deteriorate the image quality. On the other hand, according to the X-ray detector 12 of the present embodiment, because measures against the oblique incidence of an X-ray is prepared while configuring the X-ray detector 12 on the same plane, deterioration of space resolution caused by scatter rays can be reduced compared to the comparative example.

Moreover, the potential control device 120 of the X-ray detector 12 of the present embodiment applies different voltages to the plural high voltage electrodes 121a to 121e depending on a position along the cone angle direction, and thereby generates an electric field in a direction based on the cone angle. Therefore, according to the X-ray detector 12 of the present embodiment, by adjusting a distribution of potential of the plural high voltage electrodes 121a to 121e, the direction of the electric field between the high voltage electrodes 121a to 121e and the high voltage electrodes 121a to 121e can be changed according to the cone angle.

Furthermore, the method performed in the X-ray detector 12 of the present embodiment includes a potential control step of controlling respective potentials of the high voltage electrodes 121a to 121e such that the potential becomes higher as it is farther away from the center of the cone angle among the plural high voltage electrodes 121a to 121e included in the X-ray detector 12, and a reading step of reading an electric charge that is converted from the X-ray 100 by the respective plural read electrodes 123a to 123e corresponding to the plural high voltage electrodes 121a to 121e aligned in the cone angle direction of the X-ray 100. Therefore, according to the X-ray detector 12 of the present embodiment, by reading an electric charge converted from the X-ray 100 incident on a position of the corresponding high voltage electrodes 121a to 121e by the plural read electrodes 123a to 123e, it is possible to easily identify which one of the X-ray 100 that has entered from which position in the cone angle direction the electric charge that has been read by the respective read electrodes 123a to 123e is based on.

In the present embodiment, the potential control device 120 controls respective potentials of the plural high voltage electrodes 121 included in the X-ray detector 12, but the control is not limited thereto. For example, the X-ray high voltage generator 14, the controller 15, or the processing circuitry 44 of the console 40 may control the respective potentials of the plural high voltage electrodes 121. For example, the system control function 441 of the processing circuitry 44 may have a function of controlling the respective potentials of the high voltage electrodes 121.

The method of adjusting a potential distribution of the high voltage electrodes 121a to 121e is not limited to the voltage control by the potential control device 120. For example, a resistor of different value may be provided for each of the high voltage electrodes 121a to 121e. In this case, it is not necessary for the potential control device 120 to perform individual controls for the high voltage electrodes 121a to 121e. For example, the potential control device 120 simply applies a uniform voltage to the high voltage electrodes 121a to 121e. Alternatively, the X-ray detector 12 may be configured without the potential control device 120, and the power source device may apply a uniform voltage to the high voltage electrodes 121a to 121e. When such a configuration is applied, the potential control device 120 or the power source device, and the resistors arranged in each of the high voltage electrodes 121a to 121e are one example of the electric-field forming circuitry.

Second Embodiment

In the first embodiment described above, the X-ray detector 12 is provided with the plural high voltage electrodes 121a to 121e in each of the detection module 124. On the other hand, in a second embodiment, by providing a second electrode that is different from a high voltage electrode positioned on a surface of the semiconductor device 122, the direction of an electric field is adjusted to a direction along a cone angle.

Figure 6:
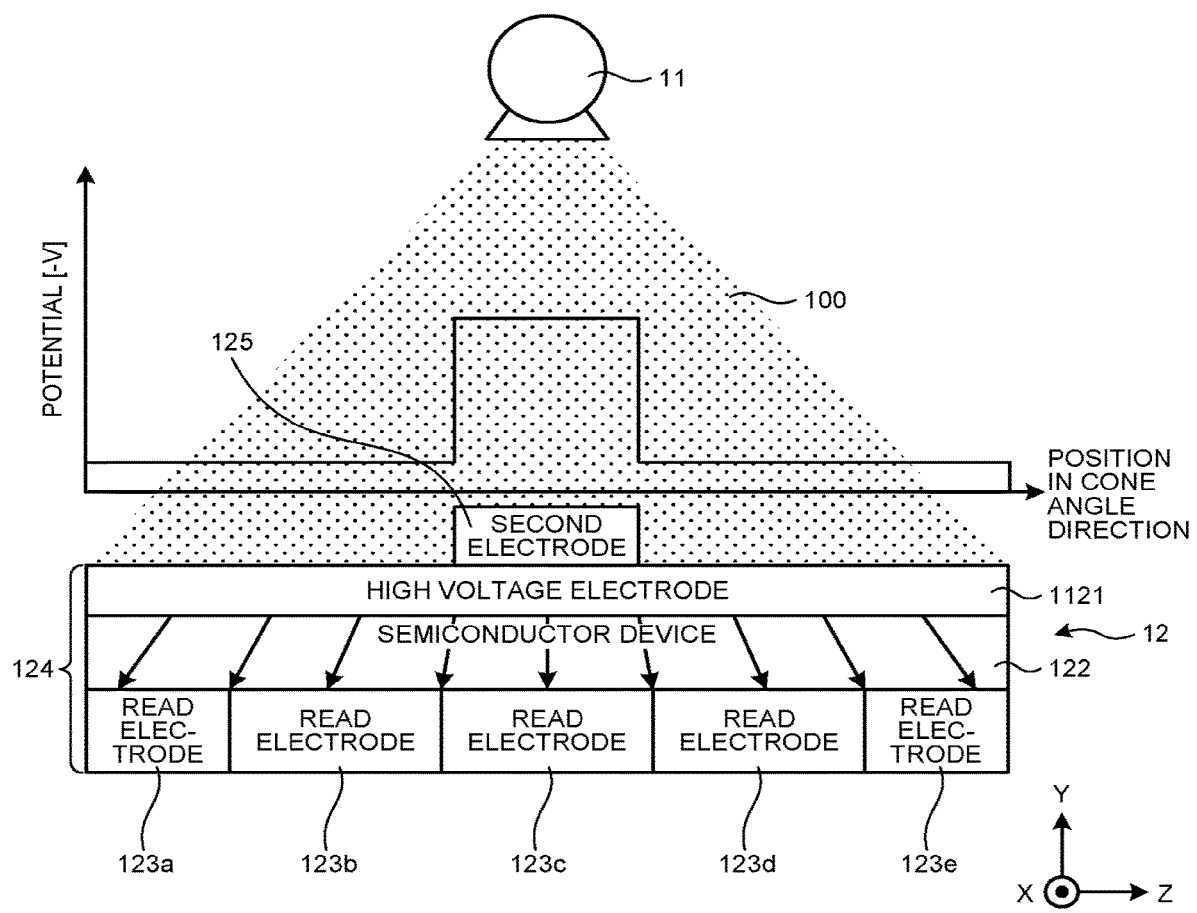
FIG. 6 is a diagram illustrating one example of a configuration of an X-ray detector according to a second embodiment.

FIG. 6 is a diagram illustrating an example of a configuration of an X-ray detector 12 according to the second embodiment. As illustrated in FIG. 2, the X-ray detector 12 of the present embodiment includes a single unit of high voltage electrode 1121, a single unit of semiconductor device 122, the plural read electrodes 123a to 123e, and a single unit of second electrode 125 in one detection module 124. The X-ray detector 12 includes the plural detection modules 50 in the fan angle direction. The number of the read electrodes 123a to 123e and the second electrode 125 included in one detection module 124 is not limited to the example illustrated in FIG. 6. When distinguishing from the second electrode 125, the high voltage electrode 1121 may be referred to as a first electrode.

In the present embodiment, a single unit of the high voltage electrode 1121 is included in each of the detection modules 124. Therefore, the high voltage electrode 1121 has a negative potential uniform in the cone angle direction. In the present embodiment, the potential control device 120 simply applies a predetermined voltage to the high voltage electrode 1121. Alternatively, the X-ray detector 12 is configured without the potential control device 120, and the power source device may apply a predetermined voltage to the high voltage electrode 1121.

The second electrode 125 is an electrode having a negative potential, and is arranged at a position overlapping the high voltage electrode 1121 in the incident direction of the X-ray 100 in at least a part of an area in the cone angle direction of the X-ray 100. A value of potential of the second electrode 125 is not particularly limited, but is lower than the potential of the high voltage electrode 1121. The high voltage electrode 1121 and the second electrode 125 are one example of the cathode electrode in the present embodiment.

Furthermore, in the present embodiment, a partial area in which the high voltage electrode 1121 and the second electrode 125 overlap is an area near the center of the cone angle as illustrated in FIG. 6. Therefore, as shown in a graph in FIG. 6, the potential of the cathode electrode near the center in the cone angle direction is lower than potentials of both ends in the cone angle direction.

Accordingly, in the present embodiment also, because of the potential difference in the cone angle direction, a direction of an electric field between the high voltage electrode 1121 and the plural read electrodes 123a to 123e is inclined so as to spread toward both end portions, similarly to the cone angle of the X-ray 100. That is, in the present embodiment also, the X-ray 100 incident on the same position in the high voltage electrode 1121 is read by the same read electrode 123 regardless of a position in a depth direction of the semiconductor device 122 at which it is absorbed.

As described, according to the X-ray detector 12 of the present embodiment, by providing plural cathode electrodes in the incident direction of the X-ray 100 in at least a part of the area in the cone angle direction, effects similar to the first embodiment can be obtained. Moreover, in the X-ray detector 12 of the present embodiment, because it is not necessary to provide plural units of high voltage electrodes in each of the detection module 124, increase in the number of parts can be suppressed.

Modification of Second Embodiment

Moreover, in the partial area in which the high voltage electrode 1121 and the second electrode 125 overlap may be the both ends portion in the cone angle direction. In this case, the second electrode 125 has, for example, a positive potential. Because the second electrode 125 makes the potential at the both end portions in the cone angle direction relatively high with respective to the center, the direction of the electric field between the high voltage electrode 1121 and the plural read electrodes 123a to 123e is inclined so as to spread toward the both end portions, similarly to the cone angle of the X-ray 100.

Moreover, the number of the second electrode 125 is not limited to one or two, but it may be three or more.

Third Embodiment

In the second embodiment described above, the second electrode 125 is arranged overlapping the high voltage electrode 1121. On the other hand, in a third embodiment, the X-ray detector 12 includes other electrodes at positions not overlapping the high voltage electrode 1121.

Figure 7:
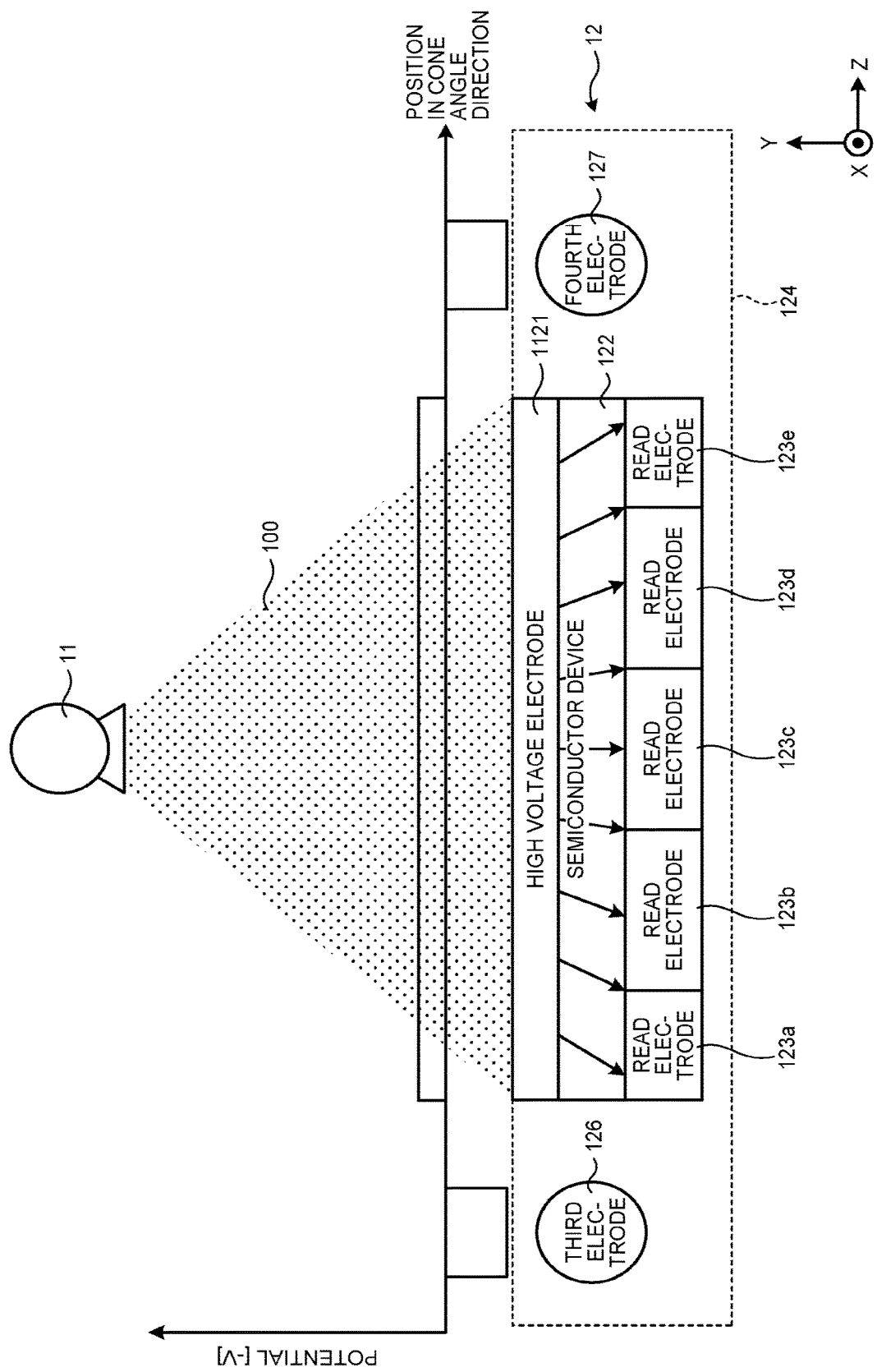
FIG. 7 is a diagram illustrating one example of a configuration of an X-ray detector according to a third embodiment.

FIG. 7 is a diagram illustrating an example of a configuration of the X-ray detector 12 according to the third embodiment. AS illustrated in FIG. 7, the X-ray detector 12 of the present embodiment includes a single unit of the high voltage electrode 1121 and a single unit of the semiconductor device 122, the plural read electrodes 123a to 123e, a single unit of a third electrode 126, and a single unit of a fourth electrode 127 in one detection module 124. The x-ray detector 12 includes plural units of the detection modules 50 in the fan angle direction.

The number of the read electrodes 123a to 123e included in one detection module 124 is not limited to the example in FIG. 6. Moreover, in FIG. 2, the X-ray detector 12 includes two additional electrodes, which are the third electrode 126 and the fourth electrode 127, the number of additional electrode is not limited to two. For example, the number of the additional electrode is one or more.

The third electrode 126 and the fourth electrode 127 are arranged at positions not overlapping the high voltage electrode 1121 and the read electrodes 123a to 123e in the cone angle direction.

The third electrode 126 and the fourth electrode 127 have a positive potential. Therefore, as shown in a graph in FIG. 7, the potentials in the high voltage electrode 1121 near the center in the cone angle direction, the third electrode 126, and the fourth electrode 127 are lower than the potential of the both end portion in the cone angle direction. Therefore, the direction of the electric field between the high voltage electrode 1121 and the read electrodes 123a to 123e tilts as it is pulled toward the both end portions.

By such a configuration, in the present embodiment also, by a potential difference in the cone angle direction, the direction of the electric field between the high voltage electrode 1121 and the read electrodes 123a to 123e has an inclination so as to spread toward the both end portions, similarly to the cone angle of the X-ray 100.

As described, according to the X-ray detector 12 of the present embodiment, by providing the third electrode 126 and the fourth electrode 127 at positions not overlapping the high voltage electrode 1121 and the read electrodes 123a to 123e in the cone angle direction, effects similar to those of the first embodiment can be obtained. Moreover, in the X-ray detector 12 of the present embodiment also, because it is not necessary to provide plural units of high voltage electrodes in each of the detection modules 124, increase in the number of parts can be suppressed.

Fourth Embodiment

In the second and the third embodiments described above, the X-ray detector 12 includes the second electrode 125, the third electrode 126, or the fourth electrode 127 different from the high voltage electrode 1121 that is positioned on a surface of the semiconductor device 122, but in the fourth embodiment, the direction of the electric field is adjusted by proving a dielectric between the high voltage electrode 1121 and the semiconductor device 122.

Figure 8:
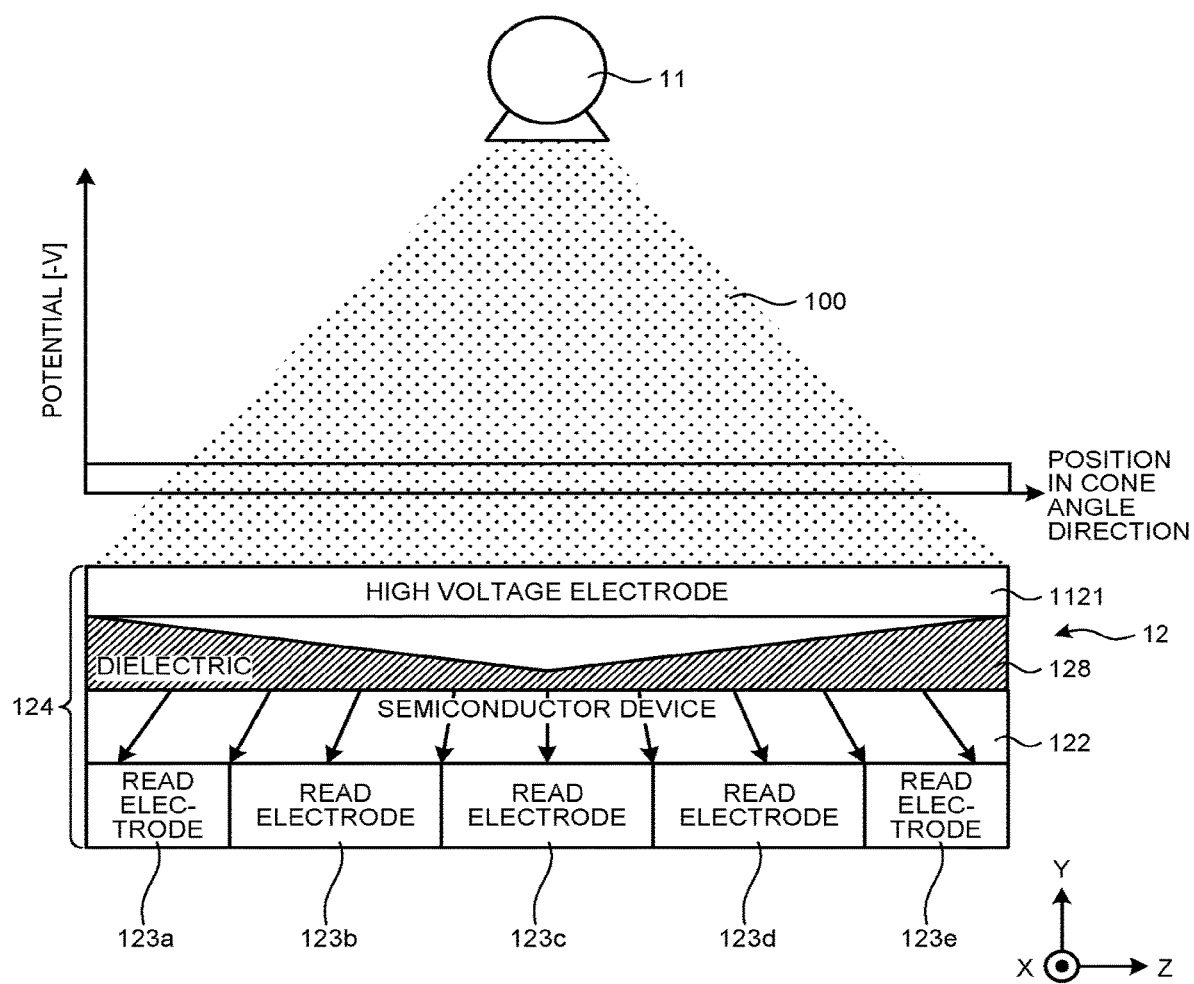
FIG. 8 is a diagram illustrating one example of a configuration of an X-ray detector according to a fourth embodiment.

FIG. 8 is a diagram illustrating an example of a configuration of the X-ray detector 12 according to the fourth embodiment. As illustrated in FIG. 8, the X-ray detector 12 of the present embodiment includes a single unit of the high voltage electrode 1121, a single unit of the semiconductor device 122, plural units of the read electrodes 123a to 123e, and a single unit of a dielectric 128 in each of the detection module 124. The X-ray detector 12 includes plural units of the detection modules 50 in the fan angle direction.

The dielectric 128 has a shape that becomes thicker as it departs away from the center of the cone angle direction of the X-ray detector 12. In the example illustrated in FIG. 8, the dielectric 128 has a wedge-shaped concave portion that symmetrically becomes thicker toward end portions from a center in the cone angle direction of the X-ray detector 12.

Because the dielectric 128 serves as a resistor of the electric field between the high voltage electrode 1121 and the read electrodes 123a to 123e, the electric field is weakened at a position at which the dielectric 128 is thicker. Therefore, in the center in the cone angle direction of the X-ray detector 12, an electric charge straight from the high voltage electrode 1121 to the read electrodes 123c is to move obliquely in a direction away from the center as it approaches the end portion in the cone angle direction. In other words, the dielectric 128 deforms the electric field to have an orientation based on the cone angle. In the present embodiment, the potential control device 120 simply applies a predetermined voltage to the high voltage electrode 1121. Alternatively, the X-ray detector 12 may be configured without the potential control device 120, and the power source device may apply a predetermined voltage to the high voltage electrode 1121. The potential control device 120 or the power source device, and the dielectric 128 are one example of the electric-field forming circuitry in the present embodiment. Alternatively, formation of an electric field includes deformation of an electric field, and the dielectric 128 alone may be one example of the electric-field forming circuitry in the present embodiment.

By such a configuration, in the present embodiment also, the direction of the electric field between the high voltage electrode 1121 and the read electrodes 123a to 123e is inclined so as to spread toward both end portions, similarly to the cone angle of the X-ray 100.

As described, according to the X-ray detector 12 of the present embodiment, because the dielectric 128 that becomes thicker as it departs away from the center in the cone angle direction is provided between the high voltage electrode 1121 and the semiconductor 122, effects similar to the first embodiment can be obtained.

Moreover, in the X-ray detector 12 of the present embodiment, because it is not necessary to provide the plural high voltage electrodes 121a to 121e, the second electrode 125, the third electrode 126, the fourth electrode 127, or the like, a high voltage supply system can be a single system, and it contributes to reduction in the number of parts and simplification of the control.

Figure 9:
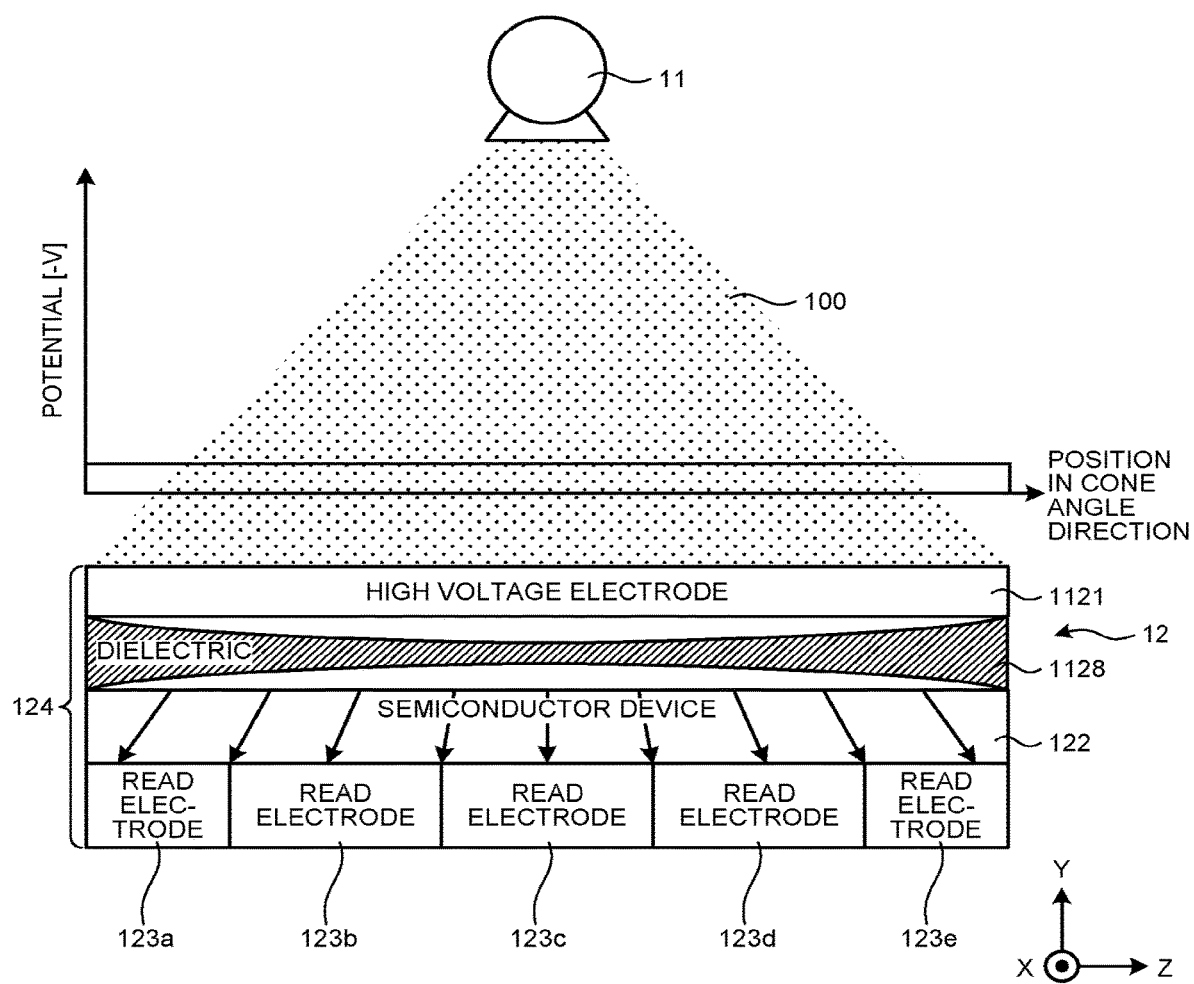
FIG. 9 is a diagram illustrating another example of a configuration of the X-ray detector according to the fourth embodiment.

The shape of the dielectric 128 is not limited to the example illustrated in FIG. 8. FIG. 9 is a diagram illustrating an example of a configuration of the X-ray detector 12 according to the fourth embodiment. As illustrated in FIG. 9, a dielectric 1128 may have a shape in which both surfaces are recessed in a hyperbolic form like a concave lens. In this case also, the dielectric 1128 has a shape in which it becomes thicker as it departs away from the center in the cone angle direction.

First Modification of First to Fourth Embodiments

In the respective embodiments described above, the X-ray detector 12 included in the X-ray CT apparatus 1 is cited as one example of the direct-conversion X-ray detector, but the direct-conversion X-ray detector is not limited thereto. For example, a flat panel detector (FPD) may be one example of the direct-conversion X-ray detector.

Second Modification of First to Fourth Embodiments

Furthermore, in FIG. 2, FIG. 6 to FIG. 9 of the respective embodiments described above, the high voltage electrodes 121a to 121e, 1121 are illustrated above and the read electrodes 123a to 123e are illustrated below, but a positional relationship between the high voltage electrodes 121a to 121e, 1121 and the read electrodes 123a to 123e is not limited thereto. For example, the read electrode may be positioned above and the high voltage electrode may be positioned below.

Various kinds of data handled in the present specification are typically digital data.

According to at least one of the embodiments explained above, deterioration of space resolution in a cone angle direction of a direct-conversion X-ray detector can be reduced.

Some embodiments have been explained, but these embodiments are presented as an example, and are not intended to limit the scope of the invention. These embodiments can be implemented in various other forms, and various kinds of omission, replacement, changes, and combination of the embodiments are possible within a range not departing a gist of the present invention. These embodiments and their modifications are included in the scope and the gist of the invention, and are, similarly, included in the scope of the invention described in claims and their equivalents.

Regarding the embodiments above, following notes are disclosed as one aspect of the invention and selective characteristics thereof.

What is claimed is:

1. A direct-conversion X-ray detector comprising:
   a plurality of anode electrodes that are aligned in a cone angle direction of an incident X-ray;
   at least one cathode electrode that is positioned on an incident side of an X-ray relative to the anode electrodes, and that opposes the anode electrodes; and
   electric-field forming circuitry configured to form an electric field in a direction based on a cone angle of the X-ray, between the anode electrodes and the cathode electrode.

2. The direct-conversion X-ray detector according to claim 1, wherein
   the electric-field forming circuitry configured to generate the electric field in a direction based on the cone angle by applying a different voltage depending on a position along the cone angle direction.

3. The direct-conversion X-ray detector according to claim 2, wherein
   a plurality of the cathode electrodes aligned along the cone angle direction are included.

4. The direct-conversion X-ray detector according to claim 2, wherein
   at least in a part of an area in the cone angle direction, a plurality of cathode electrodes are arranged in an incident direction of the X-ray.

5. The direct-conversion X-ray detector according to claim 4, wherein
   the part of an area is any one of an area near a center of the cone angle direction, and both end portions in the cone angle direction.

6. The direct-conversion X-ray detector according to claim 1, wherein
   at least one of another electrode is arranged at a position not overlapping the cathode electrode and the anode electrodes in the cone angle direction.

7. The direct-conversion X-ray detector according to claim 1, further comprising
   a semiconductor device that converts an incident X-ray into an electric charge, between the cathode electrode and the anode electrodes, wherein
   the electric-field forming circuitry is a dielectric that is positioned between the cathode electrode and the semiconductor device, and that has a shape becoming thicker as it departs away from a center of the cone angle direction.

8. A method of detecting an X-ray comprising:
   controlling a potential of each of a plurality of cathode electrodes such that a potential becomes higher as it departs away from a center of a cone angle direction out of the cathode electrodes that are included in a direct-conversion X-ray detector and that are aligned in the cone angle direction of an X-ray; and
   reading an electric charge that has been converted from the X-ray by each of a plurality of anode electrodes that are aligned along the cone angle direction of the X-ray, and that correspond to the cathode electrodes.

9. An X-ray computed-tomography apparatus comprising:
   an X-ray tube that generate an X-ray; and
   a direct-conversion X-ray detector, wherein
   the direct-conversion X-ray detector includes
      a plurality of anode electrodes that are aligned in a cone angle direction of the incident X-ray;
      at least one cathode electrode that is positioned on an incident side of the X-ray relative to the anode electrodes, and that opposes the anode electrodes; and
      electric-field forming circuitry configured to form an electric field in a direction based on a cone angle of the X-ray, between the anode electrodes and the cathode electrode.

* * * * *